(12) United States Patent
Derkx et al.

(10) Patent No.: US 10,638,978 B2
(45) Date of Patent: May 5, 2020

(54) PROCESSING DEVICE, SYSTEM AND METHOD FOR PROCESSING ACCELEROMETER SIGNALS FOR USE IN MONITORING VITAL SIGNS OF A SUBJECT

(71) Applicant: KONINKLIJKE PHILIPS N.V., Eindhoven (NL)

(72) Inventors: Rene Martinus Maria Derkx, Eindhoven (NL); Thomas Gerhard Emmrich, Gaertringen (DE); Bernd Guenter Werner Wilm, Rohrdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/551,341

(22) PCT Filed: Feb. 4, 2016

(86) PCT No.: PCT/EP2016/052328
§ 371 (c)(1),
(2) Date: Aug. 16, 2017

(87) PCT Pub. No.: WO2016/134936
PCT Pub. Date: Sep. 1, 2016

(65) Prior Publication Data
US 2018/0028121 A1 Feb. 1, 2018

(30) Foreign Application Priority Data
Feb. 26, 2015 (EP) .................................... 15156773

(51) Int. Cl.
*A61B 5/00* (2006.01)
*A61B 5/024* (2006.01)
*A61B 5/11* (2006.01)

(52) U.S. Cl.
CPC ............ *A61B 5/72* (2013.01); *A61B 5/02438* (2013.01); *A61B 5/11* (2013.01); *A61B 2562/0219* (2013.01)

(58) Field of Classification Search
CPC ......... A61B 5/72; A61B 5/02438; A61B 5/11; A61B 2562/0219
See application file for complete search history.

(56) References Cited

U.S. PATENT DOCUMENTS 9,820,680 B2 11/2017 Muzet
2002/0095087 A1 7/2002 Mourad et al.
(Continued)

FOREIGN PATENT DOCUMENTS

RU       2295910 C1    3/2007
WO    2013160538 A1   10/2013

OTHER PUBLICATIONS

Tavakolian, "Characterization and Analysis of Seismocardiogram for Estimation of Hemodynamic parameters", Ph.D. thesis, Simon Fraser University, Aug. 2010, pp. 1-193.
(Continued)

*Primary Examiner* — Catherine M Voorhees
*Assistant Examiner* — Roland Dinga

(57) ABSTRACT

The present invention relates to a processing device for processing accelerometer signals (17, 17*a-c*) for use in monitoring vital signs of a subject, comprising—a signal input unit (38) for inputting an accelerometer signal (17, 17*a-c*) of the subject in time, the accelerometer signal (17, 17*a-c*) being related to at least one physiological event being a cardiovascular or a respiratory event of the subject and measured for at least one spatial direction, an envelope determination unit (19, 40) for determining an envelope signal (21) of the input accelerometer signal (17, 17*a-c*), a calculation unit (44) for calculating an adjustment factor (43) based on an estimated time interval (45) between a first (Continued)

and a second physiological event of the subject, and a signal adjustment unit (42) for adjusting the determined envelope signal (21) by multiplying the envelope signal (21) with the calculated adjustment factor (43).

15 Claims, 12 Drawing Sheets

(56) References Cited

U.S. PATENT DOCUMENTS

| | | |
|---|---|---|
| 2005/0149136 A1 | 7/2005 | Siejko et al. |
| 2006/0020294 A1 | 1/2006 | Brockway et al. |
| 2007/0265533 A1 | 11/2007 | Tran |
| 2009/0209875 A1 | 8/2009 | Giorgis et al. |
| 2010/0331903 A1* | 12/2010 | Zhang ............... A61N 1/3621 607/5 |
| 2011/0066042 A1 | 3/2011 | Pandia et al. |
| 2012/0210513 A1* | 8/2012 | Chestakov ............ A61B 5/01 5/421 |
| 2013/0046204 A1* | 2/2013 | Lamego ............ A61B 5/4884 600/586 |
| 2013/0237873 A1 | 9/2013 | Zhang et al. |
| 2015/0065894 A1 | 3/2015 | Airaksinen et al. |

OTHER PUBLICATIONS

Crow, et al., "Relationship between seismocardiogram and echocardiogram for events in the cardiac cycle," Am. J. Noninvasive Cardiol., No. 8, pp. 39-46, 1994 (Abstract).

Eddleman, et al., "The Kinetocardiogram: I. Method of Recordings Precordial Movements," Circulation, vol. 8, pp. 269-275, Aug. 1953.

Amit, et al., "Respiratory modulation of heart sound morphology," Am. J. Physiol. Heart Circ., vol. 296, pp. 796-805, Mar. 1, 2009 (Abstract).

* cited by examiner

PROCESSING DEVICE, SYSTEM AND METHOD FOR PROCESSING ACCELEROMETER SIGNALS FOR USE IN MONITORING VITAL SIGNS OF A SUBJECT

This application is the U.S. National Phase application under 35 U.S.C. § 371 of International Application No. PCT/EP2016/052328, filed on Feb. 4, 2016, which claims the benefit of European Application No. 15156773.2, filed Feb. 26, 2015. These applications are hereby incorporated by reference herein.

FIELD OF THE INVENTION

The present invention relates to a processing device, a system and a method for processing accelerometer signals for use in monitoring vital signs of a subject. In particular, the present invention discloses a processing device, system and method for seismocardiogram signal-processing for the purpose of extracting heart-related vital sign parameters. It finds applications in patient monitoring in hospitals and at homes.

BACKGROUND OF THE INVENTION

The respiratory and heart signals and their corresponding rates are fundamental vital signs. The respiratory rate is one of the most important vital signs for patient monitors in the general ward. Usually, the respiratory and heart signals are detected through sensor electrodes attached to the person. Such signals can be generated using an obtrusive approach, which utilizes the attachment of cables, as applied to patients who are on the general ward for a significant amount of time. Alternatively, also unobtrusive measurement of respiratory and heart signals for a patient monitoring can be carried out, e.g. by using a battery-powered tri-axial accelerometer attached to a body part of the patient. In this way, seismocardiogram signals can be detected and used to determine the heart-rate and respiration-rate.

Also vibrations caused by the mechanical activity of the heart can be measured by using the ballistocardiography (BCG) technique, where the blood transport causes small changes in center-of-gravity of the person, which can be measured by measuring the small displacements of a spring-mounted bed. Alternatively, vibrations of the heart or blood-transport can be measured directly on the skin of a person via an accelerometer. The afore-mentioned techniques are known as seismocardiography (SCG). Further ways of measuring displacements on the body include kinetocardiography (KCG) and phonocardiography (using microphones in a cavity placed on the skin). It is noted that kinetocardiography and phonocardiography also relate to the measurement of the low frequencies of the anterior chest wall, similar to what is measured by using an accelerometer.

The SCG signals can be analyzed in order to detect respiratory and heart signals. For instance, two important events in a single cardiac cycle can be observed, from which one relates to aortic valve opening (AO) and the other event relates to aortic valve closing (AC). It is important to distinguish between these two events so that the vital signs are detected accurately and reliably from the SCG signals. However, processing devices and systems for SCG-signal processing known in the art are not able to output the heart-rate properly, especially when irregular heart-rates occur, for instance due to heart diseases or movement artifacts.

Pandia et al. "Motion artifact cancellation to obtain heart sounds from a single chest-worn accelerometer", 2010 IEEE International Conference on Acoustics Speech and Signal Processing (ICASSP), discloses a method of extracting primary heart sound signals from chest-worn accelerometer data in the presence of motion artifacts, wherein the proposed method outperforms noise removal techniques such as wavelet denoising and adaptive filtering.

Pandia et al. "Extracting respiratory information from seismocardiogram signals acquired on the chest using a miniature accelerometer," Physiol. Meas. vol. 33, pp. 1643-1660, 2012 discloses a method for extracting respiration signals derived from cardiac information.

US 2010/discloses a heart sound analyzer which receives electrical signal generated by a heart sound sensor, wherein the heart sound analyzer comprises an envelope extractor which processes the received signal to extract an envelope, wherein the heart sound analyzer further comprises a heart sound detector which utilizes an algorithm to detect heart sound within the envelope signal

SUMMARY OF THE INVENTION

It is an object of the present invention to provide a processing device, system and method for processing accelerometer signals for use in monitoring vital signs of a subject, which enable to provide vital signs with high accuracy and reliability, even in case of movement artifacts of the patient and/or when the patient has arrhythmias.

In a first aspect of the present invention a processing device for processing accelerometer signals for use in monitoring vital signs of a subject is presented that comprises a signal input unit for inputting an accelerometer signal of the subject in time, the accelerometer signal being related to at least one physiological event being a cardiovascular or a respiratory event of the subject and measured for at least one spatial direction, an envelope determination unit for determining an envelope signal of the input accelerometer signal, a calculation unit for calculating an adjustment factor based on an estimated time interval between a first and a second physiological event of the subject, and a signal adjustment unit for adjusting the determined envelope signal by multiplying the envelope signal with the calculated adjustment factor.

In a further aspect of the present invention a system for processing accelerometer signals for use in monitoring vital signs of a subject is presented that comprises an accelerometer for measuring an accelerometer signal of the subject in time for one or more spatial directions and a processing device as claimed herein for processing the accelerometer signal measured by the accelerometer.

In a further aspect of the present invention a method for processing accelerometer signals for use in monitoring vital signs of a subject is presented that comprises receiving an accelerometer signal of the subject in time, the accelerometer signal being related to at least one physiological event being a cardiovascular or a respiratory event of the subject and measured for at least one spatial direction, determining an envelope signal of the input accelerometer signal, calculating an adjustment factor based on an estimated time interval between a first and a second physiological event of the subject, and adjusting the determined envelope signal by multiplying the envelope signal with the calculated adjustment factor.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

The signal input unit is configured to input accelerometer signals, in particular seismocardiogram (SCG) signals, of the subject as a function of time, wherein the accelerometer signals are measured for at least one, preferably three spatial directions with reference to the patient's body. From the input accelerometer signal, the envelope determination unit is able to determine an envelope signal, which corresponds to an envelope function of the oscillating accelerometer signal outlining the upper and/or lower boundaries of the accelerometer signal.

The so-determined envelope signal is subsequently adjusted by the signal adjustment unit, which is configured to multiply the envelope signal with an adjustment factor. The adjustment factor is calculated by the calculation unit based on an estimated time interval between the first and the second physiological event of the subject, in particular a cardiovascular event or a respiratory event. The time interval may be estimated from the input accelerometer signal and/or the envelope signal determined from the input accelerometer signal. Alternatively, the time interval may be estimated from external data of the subject. The first and the second physiological event may include aortic valve opening (AO), aortic valve closure (AC), mitral valve opening (MO), mitral valve closure (MC), peak of rapid diastolic filling (RF), peak of rapid systolic ejection (RE) isotonic contraction (IC), isovolumic movement (IM) and/or peak of atrial systole (AS)

Advantageously, the adjustment factor is properly calculated, so that multiplying the envelope signal with the adjustment factor leads to an improved envelope signal. This enables to detect and monitor vital signs, in particular heart-related vital signs, with high accuracy and reliability. In particular, different physiological events of the subject that are registered in the accelerometer signal can be distinguished from each other reliably. For instance, the AO and the AC event can be distinguished from each other, so that these events can be detected from the adjusted envelope signal of the subject.

Further, the present invention enables to preserve vital signals with a relatively high signal strength level and to suppress vital signals with a relatively low signal strength level under normal conditions. In this way, the vital signs of the subject can be detected and distinguished from each other reliably.

For instance, the signal strength level of AO events is normally higher than that of the AC events. The present invention enables to preserve the AO events and effectively suppress the AC event in the adjusted envelope signal. Advantageously, the present invention is able to distinguish between the AO and AC events, even if the time difference between two adjacent heart-cycles is similar to the duration of each heart-cycle.

It is understood that the present invention is for use with, without being limited to, accelerometer and/or seismocardiogram signals. The basic principle of the present invention is also applicable to phonocardiography (stethoscopes).

Basically, all these measurements are measuring the vibrations of the skin. Using the present invention, the envelope of these vibrations can be computed to identify the events (S1, S2) or (AO, AC). Here, S1 relates to the systolic contraction and S2 relates to the end of systole.

In a preferable embodiment, the calculation unit is configured to shift the determined envelope signal in time by the estimated time interval by either a positive or negative time-lag or both. In this way, the adjustment factor can be calculated properly. Advantageously, the adjusted envelope signal is further improved.

In another preferable embodiment, the calculation unit is configured to calculate the adjustment factor using a primary function, the primary function comprising a secondary function dependent on the determined envelope signal and/or the time-shifted envelope signals. The primary and secondary functions comprise one or more algorithms which enable to obtain a highly accurate adjustment factor. Advantageously, the envelope signal can be properly adjusted.

In another preferable embodiment, the secondary function uses the determined envelope signal and/or the time-shifted envelope signals as variables and at least one predefined quantity as parameter. In this way, the value of the secondary function can be generated so long as the input accelerometer signal and/or the time-shifted envelope signals are provided to the calculation unit. The at least one predefined quantity enables to adapt the primary and the secondary function to specific adjustment requirements for adjusting the determined envelope signal. Advantageously, the adjusted envelope signal is more reliable.

In another preferable embodiment, the primary function is configured to determine a smaller value out of a computed value of the secondary function and a constant value, the calculation unit being configured to determine the adjustment factor as the smaller value. In this way, the calculation unit is able to provide a highly reliable adjustment factor based on a quantitative comparison. Advantageously, the envelope signal is effectively adjusted, so that the vital signs can be detected and monitored accurately.

In another preferable embodiment, the signal adjustment unit is configured to apply a smoothing operator to the calculated adjustment factor and multiply the determined envelope signal by the smoothed adjustment factor. The smoothing operator may be a temporal smoothing operator configured to smooth the adjustment factor temporarily. Preferably, the smoothing operator is configured to perform an asymmetric temporal smoothing, wherein the smoothing operator comprises a fast smoothing operator and a slow smoothing operator, wherein the signal adjustment unit is configured to multiply a first range of the envelope signal with increasing signal strength by the adjustment factor smoothed using the fast smoothing operator, and/or to multiply a second range of the envelope signal with decreasing signal strength by the adjustment factor smooth using the slow smoothing operator. Advantageously, this enables to suppress certain types of the detected vital signs while preserving a gradual modification or gain in an end portion or "tail" of the signal, where the envelope of the SCG signal decreases again, leading to a better maintenance of the morphology of the different types of vital signs, in particular heart-related vital signs.

In another preferable embodiment, the processing device further comprises an estimation unit for estimating the time interval between the first and the second physiological event based on the determined envelope signal. In this way, the present invention enables to estimate the time interval so that it does not rely on external estimation units. Further, the so-estimated time interval is highly accurate and reliable. Advantageously, the obtained envelope signal can be adjusted reliably.

In another preferable embodiment, the estimation unit is configured to compute an auto-correlation for the determined envelope signal. In this way, the time interval between the first and the second physiological event, in particular a first and a second cardiovascular event, is estimated accurately.

In another preferable embodiment, the estimation unit is configured to estimate the time interval between an aortic valve opening and an aortic valve closure of a heart-cycle of the subject. In this way, the adjustment factor calculated based on the so-estimated time interval is particularly suitable for adjusting the determined envelope signal. Advantageously, heart-related vital signals corresponding to aortic valve opening and aortic valve closure of the subject can be detected and reliably distinguished from each other.

In another preferable embodiment, the input unit is configured to select the accelerometer signal measured in the ventral-dorsal direction of the subject. The majority of the forces caused by the heart show in the ventral-dorsal direction of the body, so that the seismocardiogram signal measured in the ventral-dorsal direction has the highest probability of containing the most heart-related vital signs of the subject. Advantageously, the present invention is able to process accelerometer signals with high efficiency.

In another preferable embodiment, the envelope determination unit comprises a first band-pass filter for extracting a first portion of the accelerometer signal within a frequency range from a lower threshold frequency to an upper threshold frequency, an absolute-value-generator for generating an absolute value of the accelerometer signal, and/or a second band-pass filter for extracting a second portion of the accelerometer signal at frequencies higher than, equal to or lower than a cutoff-frequency. The first and/or the second band-pass filter is utilized to filter out unwanted signals. The absolute-value-generator is utilized to obtain non-negative values for the accelerometer signal. Advantageously, the envelope signal can be determined with high accuracy.

In another preferable embodiment, the processing device further comprises a peak detection unit for detecting in the determined envelope signal one or more maxima and/or minima each associated with a physiological event. Using the peak detection unit, physiological events, in particular cardiovascular events such as AO, AC, MO, MC, RE and RF can be detected. Advantageously, the corresponding vital signs can be effectively monitored.

In another preferable embodiment, the processing device further comprises a classification unit for classifying a peak detection result by deriving one or more classification features from the determined envelope signal. The one or more classification features may comprise the maximum or mean amplitude of the envelope signal, the mean and variance of the peak-to-peak intervals as being detected by the peak detector and the similarity in morphology of multiple heart-cycles from the envelope signal in combination with the peak detection results. When looking at similarity of multiple heart-cycles, it can be beneficial to distinguish between the heart-cycle morphologies during premature ventricular contractions (like in Trigenimy arrhythmias) versus regular heart-cycle morphologies. Advantageously, the present invention enables to reliably distinguish between peaks of different heart-cycles, so that the reliability of the monitored vital signs of the subject is further increased.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

The respiratory and heart signal and its corresponding rates are fundamental vital signs. The respiratory rate is one of the most important vital signs for patient monitors in a general ward. Usually, the vital signals are generated through sensor electrodes attached to the person, as is the case using electrocardiogram (ECG). However, as many patients spend a significant amount of time on the general ward, the ECG-based solution utilizing attachment of cables are normally obtrusive, meaning that the sensor electrodes are in direct contact with the patient, e.g. the skin of a body part.

Figure 1:
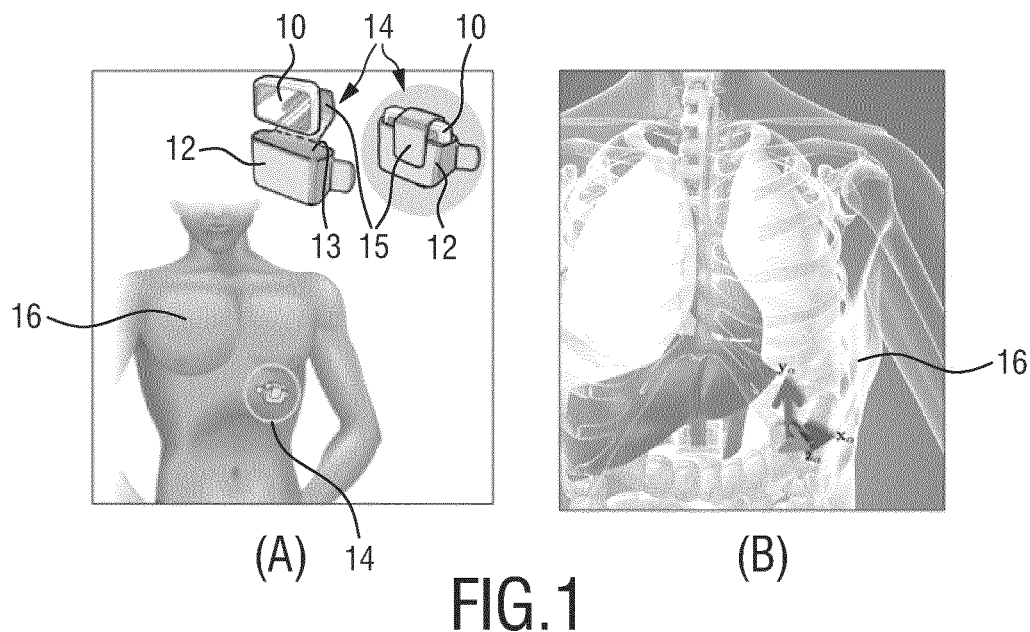
FIG. 1 shows a schematic representation of a monitoring system for monitoring vital signs of a patient, wherein the monitoring system is attached to the body of the patient.

Respiratory and heart signals can also be monitored using an unobtrusive solution, for instance, by means of a battery-powered tri-axial accelerometer attached to the body of the patient, as shown in FIG. 1. FIG. 1A shows illustratively an embodiment of a monitoring system 10 for processing seismocardiogram signals for use in monitoring heart-related vital signs. The monitoring system 10 comprises an accelerometer and a processing device, which will be explained in more detail later. The monitoring system 10 is carried by an attaching means 12 which functions as a case for the monitoring system 10 in order to form a portable system 14. As shown in FIG. 1A, the monitoring system 10 can be detachably introduced into the inner part of the attaching means 12 via an opening 13. After loading, a belt-like closing means which is fastened to the attaching means on one side, can be used to lock the monitoring system 10 by connecting the other side of the belt-like closing means 15 to the attaching means 12.

The portable system 14 is detachably attachable to the patient. FIG. 1B shows a Cartesian coordinate system with respect to the portable system 14 attached to the patient 16 in FIG. 1A.

Figure 2:
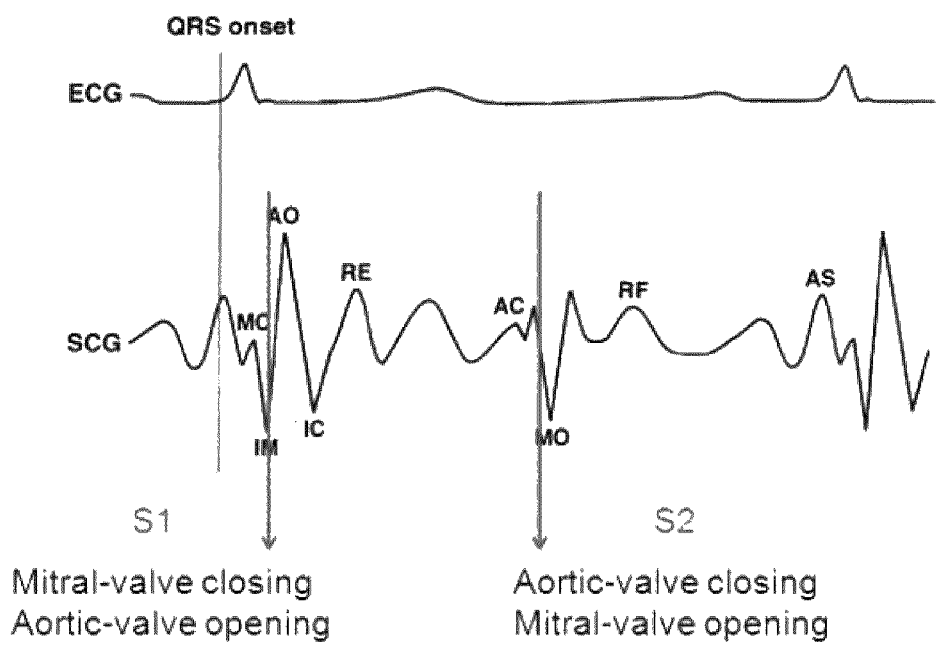
FIG. 2 shows an example of a seismocardiogram (SCG) signal compared to an electrocardiogram (ECG) signal.

Using the monitoring system 10, seismocardiogram signals can be measured in order to determine the heart-rate of the patient. In particular, the vibrations of the heart or blood-transport can be directly measured using the accelerometer of the monitoring system 10. FIG. 2 shows an SCG signal as disclosed in Crow et al., "Relationship between seismocardiogram and echocardiogram for events in the cardiac cycle", Am. J. Noninvasive Cardiol., no. 8, pp. 39-46, 1994. In particular, an exemplary SCG signal (lower graph) compared to an exemplary ECG signal is shown in FIG. 2. The SCG signal has been averaged from a plurality of measurement results. The ECG signal can be used to segment the SCG signal into different portions. In this case, it is advantageous to use an ECG signal which has been measured simultaneously to the SCG signal.

As shown in FIG. 2, a plurality of cardiovascular events can be extracted from the SCG signal by detecting the corresponding peaks and/or valleys. For instance, the cardiovascular events aortic valve opening (AO), aortic valve closing (AC), mitral-valve closing (MC) and mitral-valve opening (MO) can be extracted from the SCG signal by detecting their corresponding peaks. The AO- and the MC-peaks are located within an oscillation region S1, wherein the AC- and MO-peaks are located within another oscillation region S2, as shown by the arrows in FIG. 2. In particular, the Si oscillation relates to the systolic contraction and the S2 oscillation relates to the end of systole.

Figure 3:
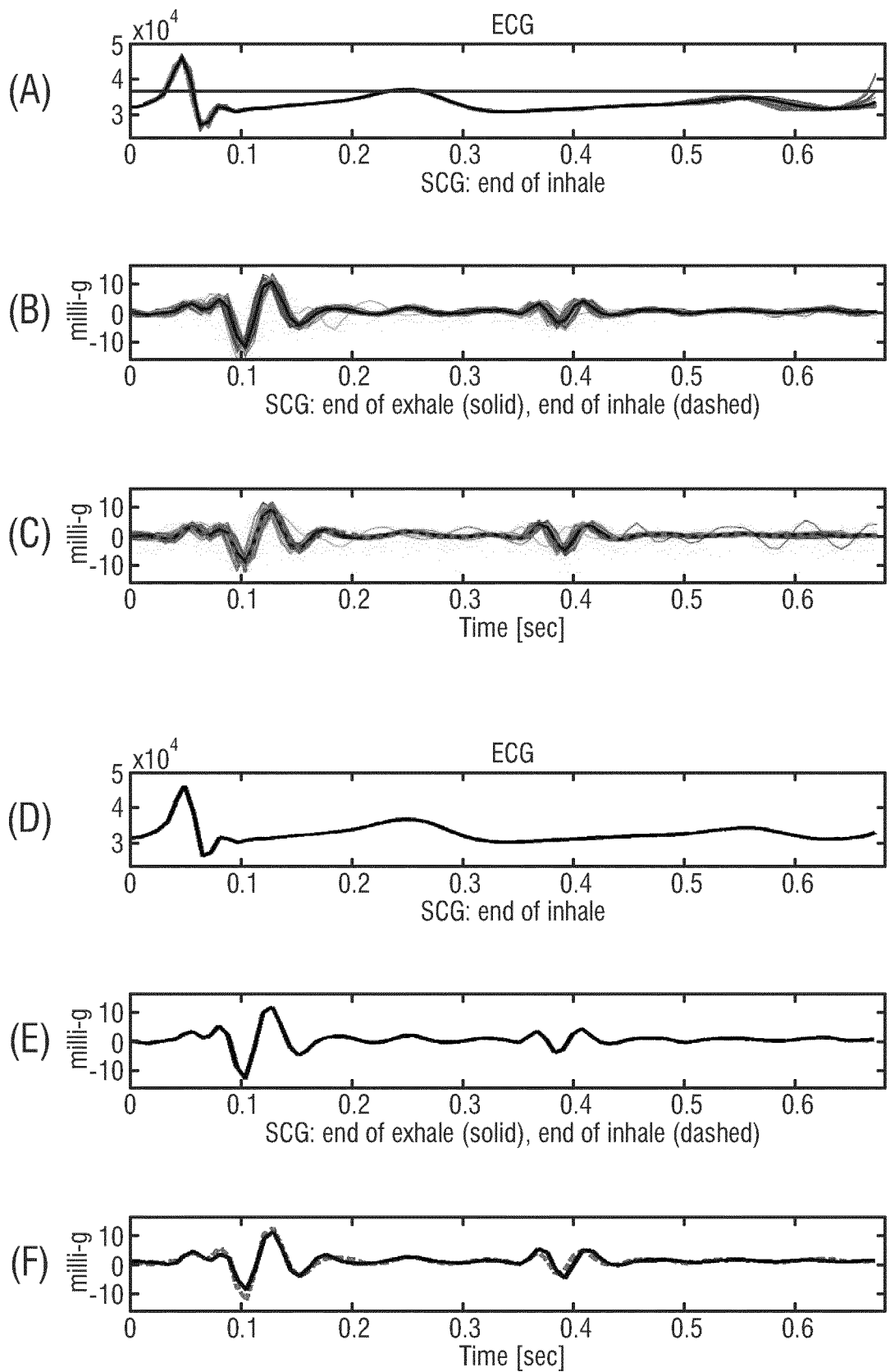
FIG. 3A-F show further examples of seismocardiogram signals.

FIG. 3 shows another example of SCG measurements compared with an ECG measurement. In FIG. 3A, a plurality of ECG signals are shown for a patient lying in a supine position over a time period of 700 ms. Here, an R-peak can be seen within the first 100 ms, followed by the T-peak at approximately 250 ms and finally the P-peak of the next heart-cycle visible and approximately 550 ms. The letters Q, R, S, T and P indicate a Q-wave, R-wave, S-wave, T-wave, and P-wave detected in the ECG signal. As there is a typical variation in the heart-cycles related to the R-R periods, only the initial part of the measurement, i.e. the first 700 ms of the heart-cycle starting with time 0 at which an ORS complex is visible is shown.

The ECG signal is preferably used to segment the accelerometer data in FIG. 3B and FIG. 3C, wherein only the accelerometer data for the z-axis corresponding to the ventral-dorsal direction perpendicular to the skin of the patient is shown, measured for the same time period as the ECG signal in FIG. 3A. Further, the SCG signal has been filtered using a band-pass filter so that only the signal portion within a frequency range from 10 to 40 Hz is taken into account.

In FIG. 3B, a plurality of SCG signals are shown for the end of an inhale. A plurality of peaks corresponding to the cardiovascular events AO, AC, MO and MC can be seen in the results. In FIG. 3C, SCG signals measured at the end of an exhale, in addition to the SCG signals shown in FIG. 3B.

The SCG signals measured at the end of the exhale are shown as solid curves, whereas the SCG signals measured at the end of inhale are shown as dashed curves. It is distinguished between the averaging process between two phases, namely the end of an inhale and the end of an exhale. For this differentiation, a respiratory inductive plethysmography (RIP) band, hereafter called 'respiband', is used to capture the respiration signal (indicative for the respiratory volume) of the patient.

In FIG. 3D, an averaged ECG signal averaged from the plurality of ECG signals shown in FIG. 3A is shown. In FIG. 3E, an averaged SCG signal averaged from the plurality of SCG signals shown in FIG. 3B is shown. In FIG. 3F, an averaged SCG signal averaged from the plurality of SCG signals shown in FIG. 3C is shown. In FIG. 3D-F, it can be seen that during the end of the inhale the AO will be larger and the AC will be smaller compared to the end of the exhale. Hence, the ratio AO/AC peaks will be indicative of the respiratory phase.

The results in FIG. 3A-F show a high correspondence with the results of Crow et al., as shown in FIG. 2.

Figure 4:
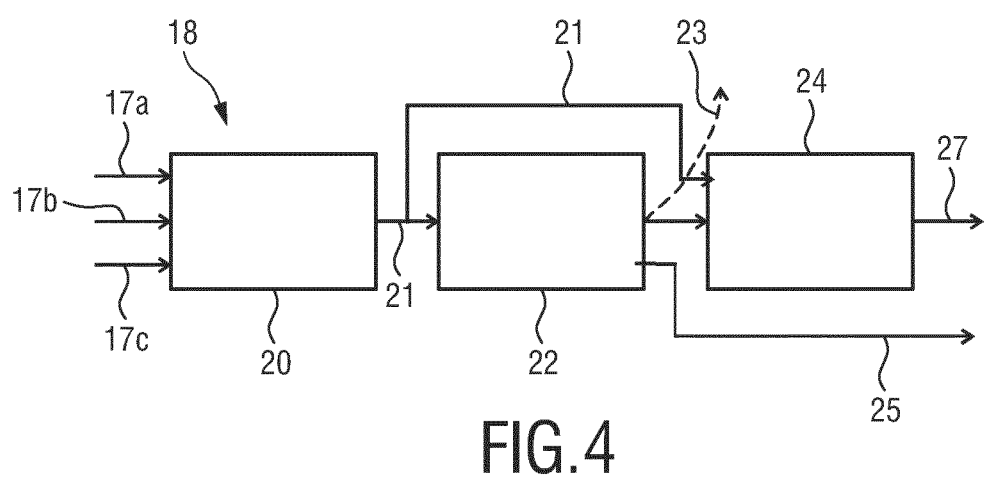
FIG. 4 shows a schematic block diagram of a processing device according to an embodiment.

FIG. 4 shows a processing device 18 for processing accelerometer signals for use in monitoring heart-related vital signals for a subject. The processing device 18 comprises a pre-processing unit 20, a peak detection unit 22 and a classification unit 24. The pre-processing unit is configured to receive an accelerometer signal measured for at least once, preferably three spatial directions mentioned above in FIG. 1B. As shown in FIG. 4, the seismocardiogram signals 17a-c for the three spatial directions x, y and z with respect to the monitored subject are received by the pre-processing unit 20. The pre-processing unit 20 comprises an envelope determination unit 19 (FIG. 7) for determining an envelope signal 21 of the input accelerometer signals 17a-c. The peak detection unit 22 is configured to detect one or more maxima and/or minima in the determined envelope signal 21, each maximum and/or minimum being associated with a cardiovascular event. For instance, the peak detection unit 22 may be configured to detect an AO event in the envelope signal 21.

After detecting the one or more maxima and/or minima, a data set containing the maxima/minima associated with the corresponding cardiovascular events (indicated by the dashed arrow 23') may be output. Further, a new data set comprising the envelope signal 21 and one or more indicators indicating the cardiovascular events associated with the maxima/minima can be output (as shown by arrow 25) for deriving a vital sign, such as a heart-rate.

Furthermore, from the cardiac events, also the respiration-rate can be derived; it is known from 'K. Pandia, O. T. Inan, G. T. A. Kovacs, and L. Giovangrandi, "Extracting respiratory information from seismocardiogram signals acquired on the chest using a miniature accelerometer," *Physiol. Meas.* vol. 33, pp. 1643-1660, 2012.' that respiration information can be obtained via the AO, AC, MO and MC events.

Figure 5:
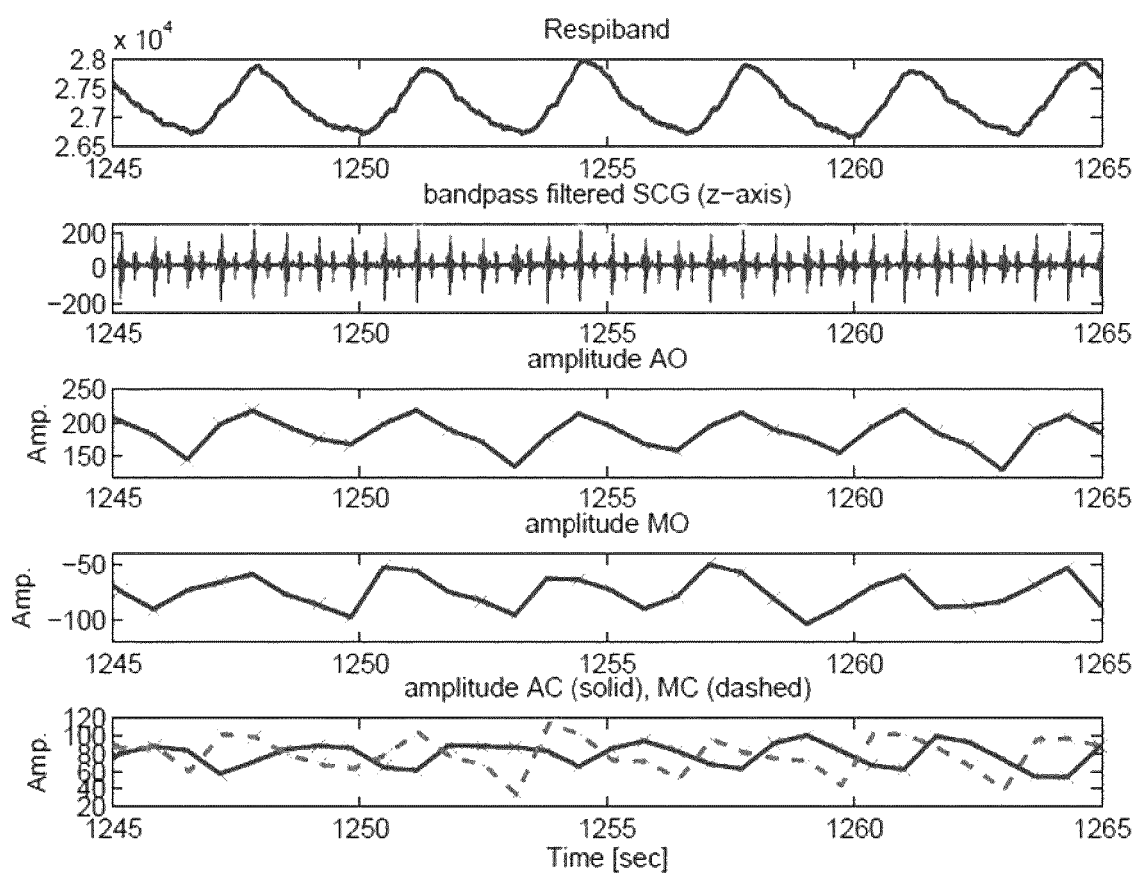
FIG. 5 shows exemplary measurement results of modulation of amplitudes of seismocardiogram signals.

When looking at the modulation of amplitudes of these events, we can show via the example in FIG. 5 that a respiration-wave can be derived.

Figure 6:
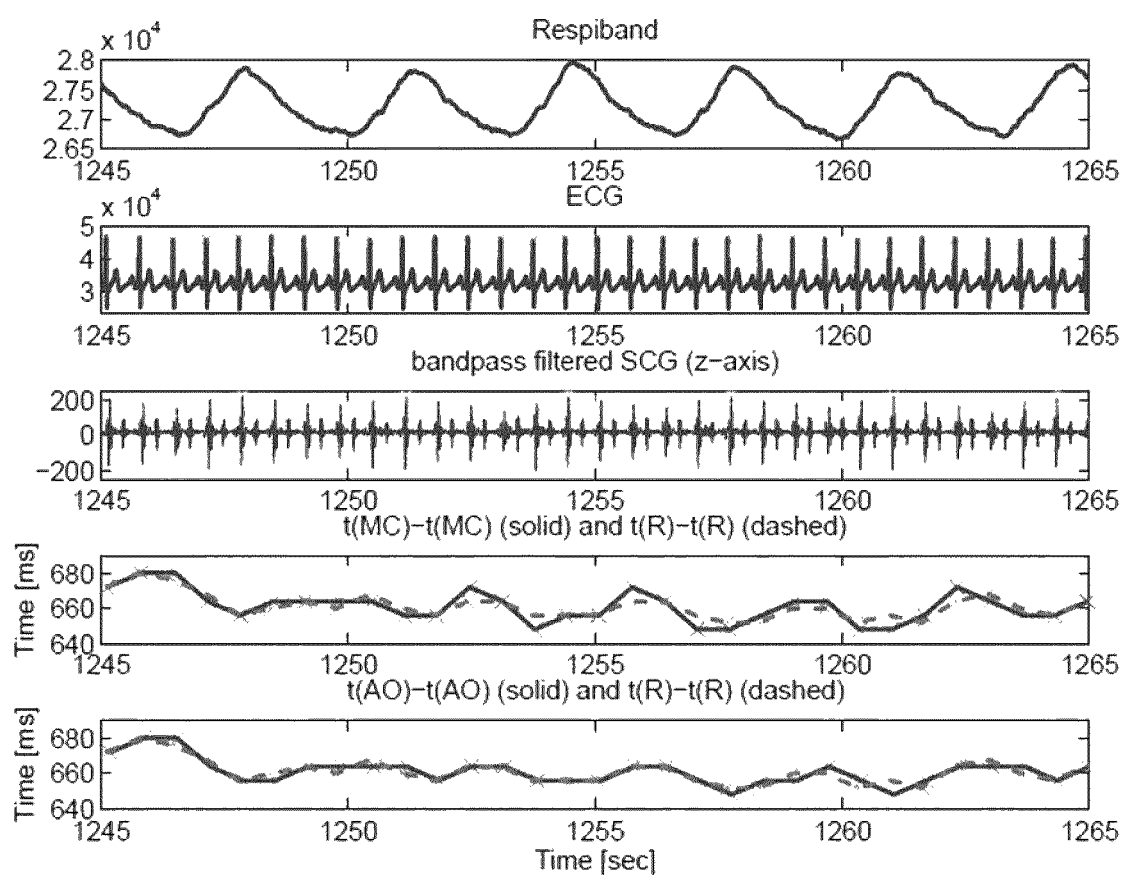
FIG. 6 shows exemplary measurement results of modulation of time-differences of seismocardiogram signals.

Not only the modulation of the peaks of the cardiac events give information regarding the respiration-rate; also the modulation in time-differences of the cardiac events are known to provide information about the respiration-rate. This is shown in FIG. 6. Both the modulation of time-differences and amplitudes of cardiac events are indirect measurements of the respiration-rate. They should be combined with direct measurements of the respiration-rate by the accelerometer. More specifically, the tilt of the accelerometer will be a direct measurement of the chest movement. However, this is outside the scope of our invention.

Preferably, the envelope signal 21 and a data set 23 containing the maxima/minima associated with the corresponding cardiovascular events are further processed by the classification unit 24, which classifies the peak detection result by deriving one or more classification features from the envelope signal 21. In particular, the classification unit 24 computes the one or more classification features based on a portion of the envelope signal 21 with a predefined time length, e.g. eight seconds, and classifies the peak detection result as being either "good" or "bad". For instance, when the monitored subject has shown severe movements artifacts, corresponding motion features may be derived by the classification unit 24, which preferably classifies the envelope signal with its corresponding peak-detections in the eight seconds window as "bad". Consequently, the envelope signal determined for these time window and/or the accelerometer signal input for these time window will be classified as "bad". The labeling of the classification may be output as indicated by arrow 27.

Preferably, the classification unit 24 is configured to classify the peak detection result based on a wave-shape model. In particular, the similarities in morphology in a heart-cycle are utilized. It is noted that the term "peak" refers to both maximum and minimum within the scope of the present application.

Figure 7:
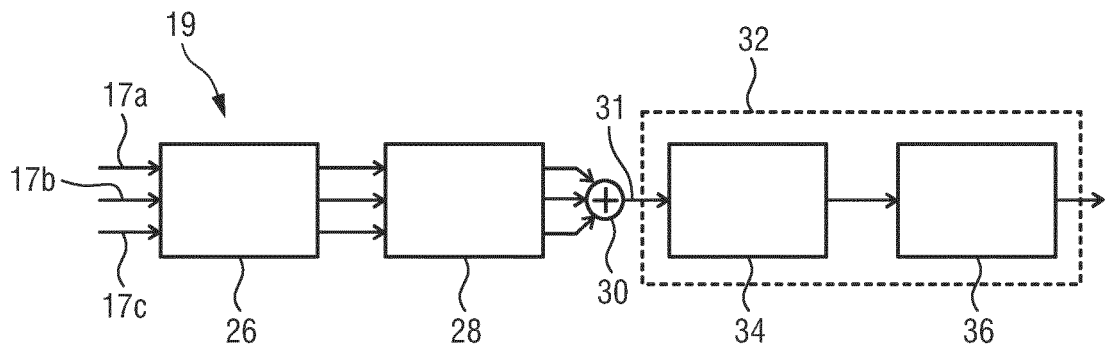
FIG. 7 shows a pre-processing unit of the processing device in FIG. 4.

FIG. 7 discloses an envelope determination unit 19 of the pre-processing unit 20 of FIG. 4. The envelope determination unit 19 comprises a band-pass filter (BPF) 26 for extracting a portion of the accelerometer signal 17a-c within the frequency range. Preferably, the BPF 26 is configured to filter out the signals related to breathing with mainly low frequencies up to 5 Hz by choosing an upper threshold frequency of 40 Hz and a lower threshold frequency of 10 Hz. Subsequently, the band-pass filtered accelerometer signals 17a-c, each representing a spatial direction or axis, are processed by an absolute-value-generator 28, which computes the absolute value for each of the three axes.

The absolute values of the accelerometer signals 17a-c, which are considered each as a SCG signal, are then added together by a summator 30, resulting in one single accelerometer signal 31. The accelerometer signal 31 is subsequently forwarded to an envelope filter 32, which comprises a low-pass filter (LPF) 34 and optionally also a high-pass filter (HPF) 36 to remove the baseline (DC) signal. The LPF 34 is configured to extract a portion of the SCG signal at frequencies lower than a cutoff-frequency, wherein the HPF 36 is configured to extract a portion of the SCG signal at frequencies higher than a cutoff-frequency (equal to or lower than, equal to or higher than) Preferably, the cutoff-frequencies of the LPF 34 and/or the HPF 36 can be varied depending on the expected range of heart-rate for particular patient groups. For example, younger age-groups will preferably have higher cutoff-frequencies. Using the envelope filter 32, the envelope of the SCG signal 31 can be computed.

Figure 8:
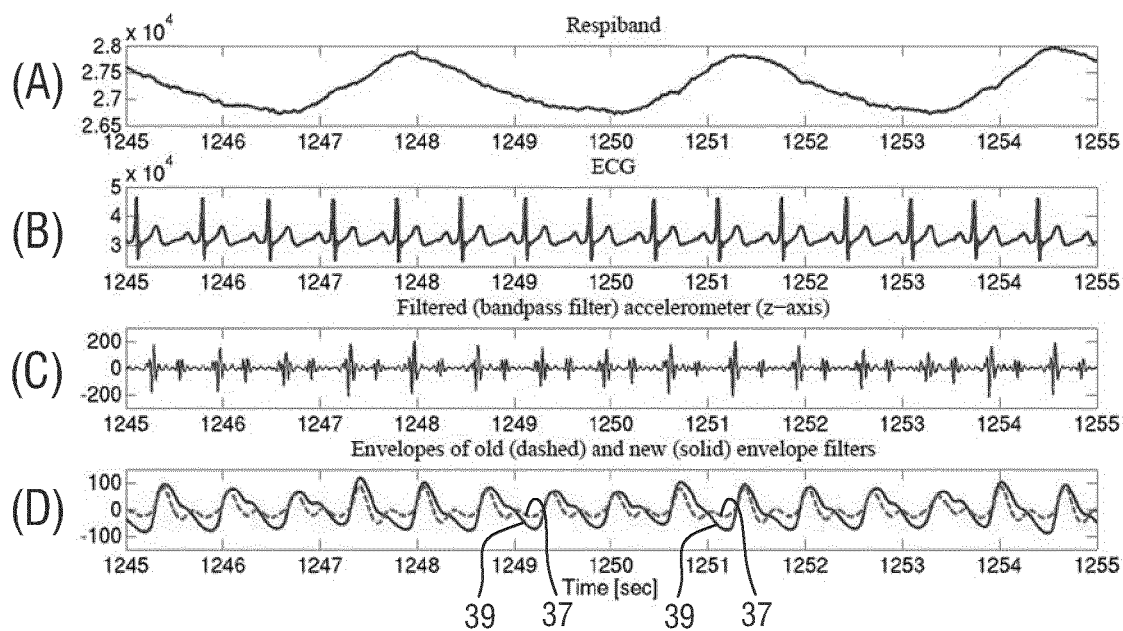
FIGS. 8A-D show exemplary measurement results of seismocardiogram signals.

FIG. 8 shows the results of four different measurements for the same time window. FIG. 8A shows a respiband signal. The respiband signal shows oscillatory behavior. FIG. 8B shows an ECG signal of the same patient. FIG. 8C shows a band-pass filtered accelerometer signal for the z-axis corresponding to the SCG signal 17c in FIG. 9 after passing the BPF 26. Here, measurement of the respiration-rate via the modulation (in time and/or amplitude) of the AO and AC events is shown, wherein the ratio AO/AC gives information about the respiration rate. FIG. 8D shows a first envelope signal (dashed curve) and a second envelope signal (solid curve), wherein both envelope signals have been determined using the envelope determination unit 19 in FIG. 9. In particular, the cutoff-frequency of the LPF 34 is lowered for the second envelope signal (solid curve) compared to the first envelope signal (dashed curve) as can be seen in FIG. 8D, both envelope signals show oscillatory behavior with a plurality of periodic maxima and minima, including the minima 37 of the first envelope signal and the minima 39 of the second envelope signal. The minima 37, 39 correspond to the AC event. As can be seen from FIG. 8D, the minima 39 of the second envelope signal are significantly lower in amplitude than the minima 37 of the first envelope signal, indicating that the AC event in the second envelope signal is more strongly suppressed compared to the first envelope signal, due to the lower cutoff frequency of the LPF 34.

Figure 9:
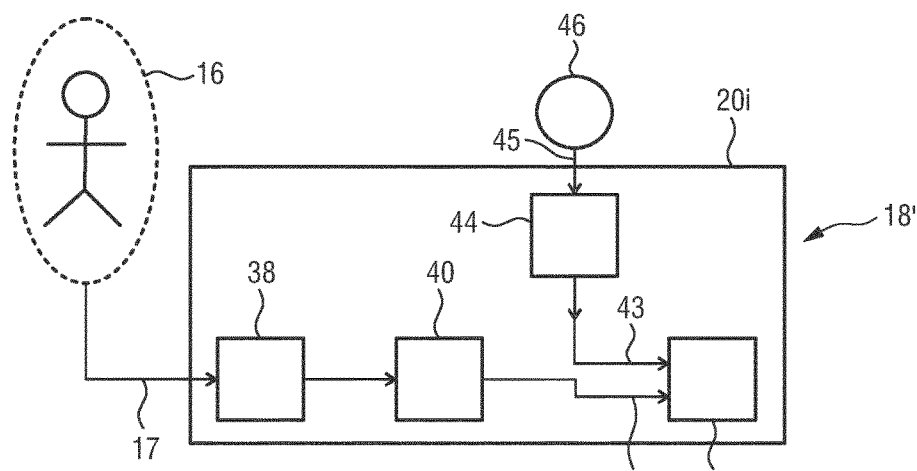
FIG. 9 shows a processing device according to another embodiment.

FIG. 9 shows another processing device 18' comprising a pre-processing unit 20i, wherein the pre-processing unit 20i comprises a signal input unit 38, an envelope determination unit 40, a signal adjustment unit 42 and a calculation unit 44. An SCG signal 17 measured from the subject 16 is input the signal input unit 38 and subsequently processed by the envelope determination unit 40 which may be the envelope determination unit 19 shown in FIG. 9 and determines an envelope signal 41. The envelope signal 41 is subsequently adjusted by the signal adjustment unit 42 in order to generate an adjusted envelope signal. For this purpose, the envelope signal 41 is multiplied by an adjustment factor 43 which is calculated by a calculation unit 44 based on an estimated time interval 45 between a first and a second cardiovascular event of the subject 16. The time interval 45 is estimated by an estimation unit 46. In the embodiment shown in FIG. 9, the estimation unit 46 is arranged separately from the processing device 18'. Alternatively, the processing device 18' may include the estimation unit 46.

Figure 10:
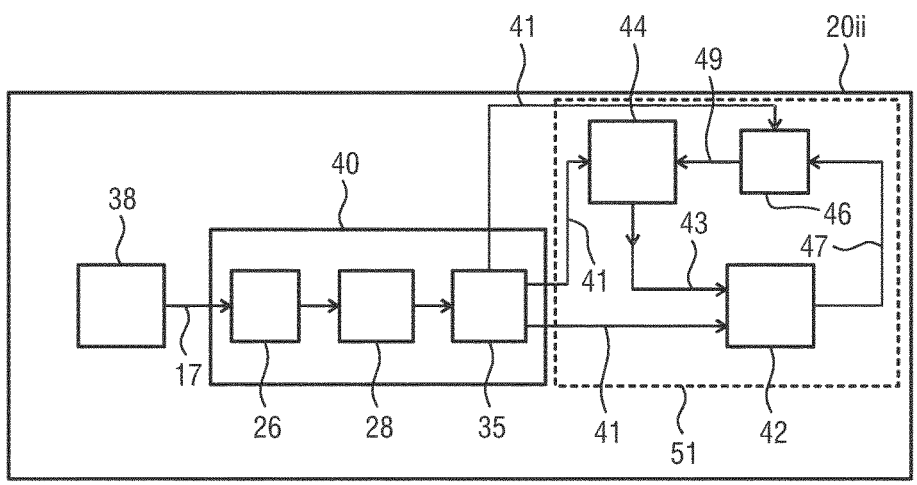
FIG. 10 shows a further pre-processing unit according to another embodiment.
Figure 10:
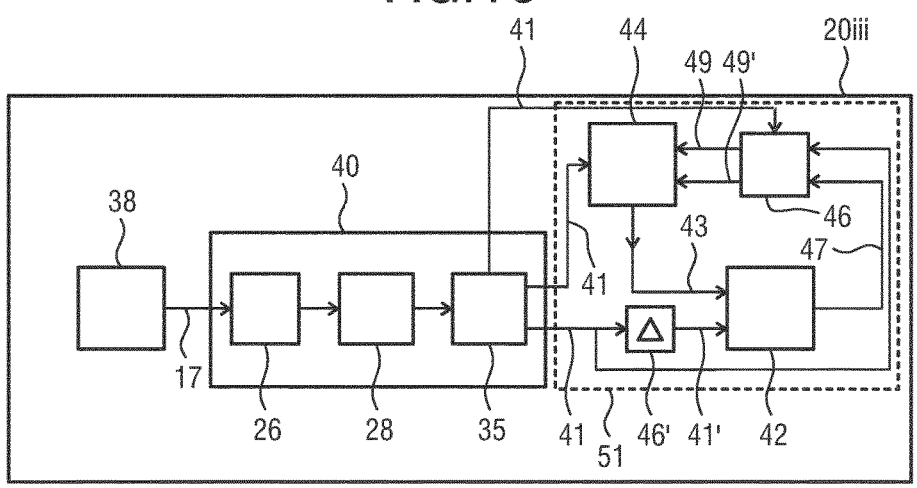

FIG. 10 shows an alternative pre-processing unit 20ii for the processing device 18' in FIG. 9. The envelope determination unit 40 comprises the band-pass filter 26 and the absolute-value-generator 28 as specified under reference of FIG. 9. Further, the envelope determination unit 40 comprises a low-pass filter 35. The SCG signal 17 inputs to the signal input unit 38 is band-pass filtered by the band-pass filter 26. Preferably, the SCG signal 17 comprises an accelerometer signal for the z-axis only, wherein the z-axis corresponds to the ventral-dorsal direction of the subject 16. Further preferably, the frequency range of the BPF 26 is chosen as from 10 to 40 Hz. Then, the band-pass filtered SCG signal is processed by the ABS 28, before being processed by the LPF 35. The LPF 35 is configured to extract the envelope signal 41 from the absolute value of the band-pass filtered SCG signal using a cutoff-frequency, preferably 8 Hz. In this way, the signal parts, in particular the peaks corresponding to the AO and AC events are well maintained in the envelope signal 41.

The envelope signal 41 is subsequently adjusted by the signal adjustment unit 42, which multiplies the envelope signal 41 with the adjustment factor 43. The adjustment factor 43 is calculated by the calculation unit 44. In particular, the calculation unit 44 calculates the adjustment factor 43 based on the envelope signal 41 determined by the envelope determination unit 40. Further, the adjustment factor 43 is calculated based on a time-shifted envelope signal 49, wherein the time-shifted envelope signal 49 is obtained by delaying the envelope signal 47 adjusted from the signal adjustment unit 42 by the time interval 45 using the estimation unit 46. The estimation unit 46, which is integrated in the pre-processing unit 20ii in FIG. 10, estimates the time interval based on the envelope signal 41 provided by the LPF 35.

Figure 11:
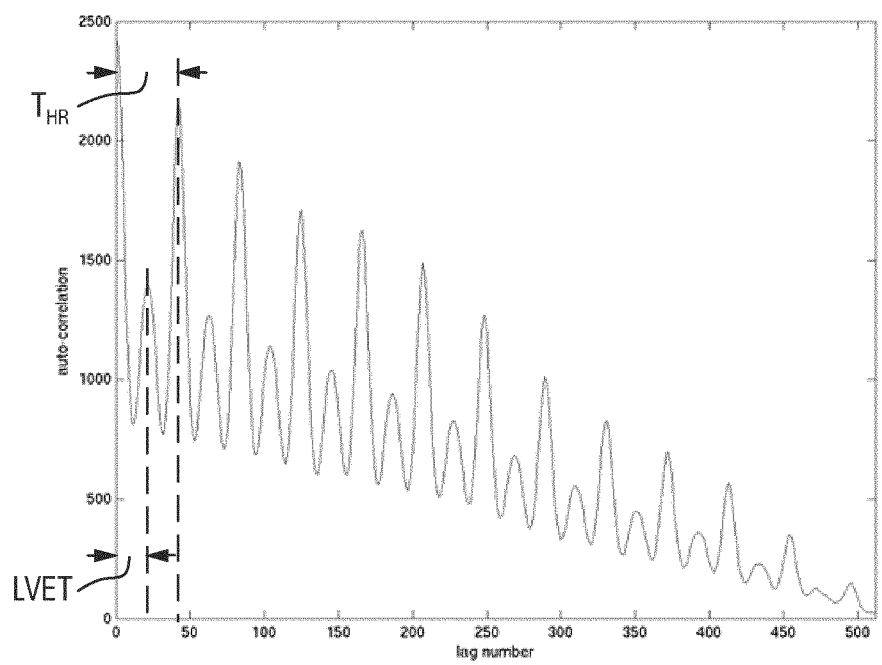
FIG. 11 shows an exemplary auto-correlation for estimating a time-interval between two cardiovascular events.

Preferably, the time interval 45 is estimated using an auto-correlation of the SCG envelope 41. Further preferably, the time interval 45 is estimated being a left ventricular ejection time (LVET), which is the time interval between an AO event and a subsequent AC event within the same heart-cycle. An exemplary auto-correlation signal is shown in FIG. 11, where the auto-correlation is computed for a time window of eight seconds, wherein the time is indicated by the lag number. The auto-correlation signal is computed using input signals sampled at 62.5 Hz; this means that a lag number of 125 is equivalent to 2 seconds. As can be seen in FIG. 11, the auto-correlation decreases starting from lag number 0. After the first minimum, the auto-correlation increases again and the first local maximum lies at the lag number 20, which corresponds to approximately 320 ms in time. The time interval between the lag number 0 and the lag number 20 is determined as the LVET. The next peak of the auto-correlation appears at a lag number of approximately 42, as indicated by the second dashed line, wherein the time interval between the lag number 0 and the second peak at lag number 42 corresponds to the heart-rate period $T_{HR}$, which is the reciprocal value of the heart-rate. Hence, an algorithm to find the LVET can be based on finding the first local maximum starting from lag number 1. It is noted that in this particular example the heart-cycle is constant over time, which results in a clear increase at lag 42. However, when we have a situation with irregular heart-rates, this does not have to be the case.

After the envelope signal 47 has been delayed in time by the amount of the estimated time interval 45, which results in the time-shifted envelope signal 49, the calculation unit 44 preferably uses a primary function to calculate the adjustment factor 43. In particular, the primary function has the following form:

$$G = \min\{f(x, y_A), c\} \quad (1)$$

f (x, $y_A$) is a secondary function, wherein x represents the envelope signal 41 determined from the envelope determination unit 40 and $y_A$ represents the time-delayed envelope signal 49 provided by the estimation unit 46. Preferably, the primary function G is a gain function, wherein the secondary function f (x, $y_A$) has the following form:

$$f(x, y_\Delta) = \frac{x}{\gamma \cdot y_\Delta + \varepsilon} \quad (2)$$

The quantities ε and γ are predefined parameters, wherein ε is chosen to prevent the secondary function f from having a denominator equal to 0, and γ is chosen for setting the amount of suppression of the envelope signal for a particular cardiovascular event. Preferably, the value of γ is equal or larger than 1.

In a preferable embodiment, the quantity $y_A$ represents the envelope signal 49 delayed by the LVET. The primary function G (x, $y_A$) therefore uses the quantities x and $y_A$ as variables and the quantities γ and ε as predefined constant parameters. In particular, the primary function G (x, $y_A$) is configured to determine a smaller value out of the computed value of the secondary function f (x, $y_A$) and the constant value c, wherein c is preferably equal to 1. The so-determined smaller value out of the computed value of the secondary function f (x,$y_A$) and the constant value c, c being preferably equal to 1, will be chosen as the adjustment factor 43. In the following, the way of function of the processing device 18' in FIG. 9, in particular the pre-processing unit 20i, 20ii, will be discussed using the cardiovascular events AO and AC as an example. When detecting SCG signals for monitoring heart-related vital signals, it is desirable that the peak corresponding to the AC event is suppressed in the envelope signal compared to a peak corresponding to the AO event, since this corresponds to the normal heart-rate behavior and enables a reliable determination of the subject's heart-rate. For the case, in which the envelope signal 47 effectively shows preserved peaks corresponding to the AO events while showing suppressed peaks corresponding to the AC events, the quantity $y_A$ representing the envelope signal 49 delayed by the LVET contains the peaks for the AO event in the same time windows as the quantity x, which represents the envelope signal 41 before adjustment, contains the peaks for the AC events. This is based on the assumptions that the LVET remains essentially constant during the measurement and that the peaks for the AO events have higher signal strength compared to the AC events. The latter assumption is, however, not always fulfilled, since an AO peak without a significant cardiac output may occasionally be detected, e.g. when the patient has arrhythmia's.

As a result, the value of the gain function G (x, $y_A$) is close to 0, resulting in an adjusted envelope signal 47 effectively suppressing the peaks corresponding to the AC events. In a preferable embodiment, the value of the gain function G (x, $y_A$) can be temporarily smoothed before being multiplied with the envelope signal 41. For instance, an asymmetric temporal smoothing may be applied which consists of a fast smoothing and a slow smoothing, wherein the adjustment factor smoothed using the fast smoothing is applied to adjust the envelope signal 41 in a first region, in which the signal strength of the envelope signal 41 increases. Further, the adjustment factor smoothed using a slow smoothing is applied to adjust the envelope signal in a region, in which the signal strength of the envelope signal decreases. Further preferably, the slow smoothing utilizes a time constant and/or a memory amount larger than that utilized in the fast smoothing. Advantageously, the AC peaks can be effectively suppressed in the adjusted envelope signal while a gradual modification or gain in the "tail" of the adjusted envelope signal is still preserved, leading to an improved maintenance of the morphology of the peaks for the AO events and residual AC events in the envelope signals.

In the time windows, in which the quantity x representing the envelope signal 41 before adjustment contains peaks for the AO event, the quantity $y_A$ representing the envelope signal 47 delayed by the LVET is small so that the value of the gain function G (x,$y_A$), hence the adjustment factor, will be equal to 1. The reason why the quantity $y_A$ is small is because of the feedback loop 51 in the pre-processing unit 20ii of FIG. 10. This means that even if the time difference between the AC event of a first heart-cycle and the AO event of subsequent heart-cycle is close to or exactly equal to the LVET-time, the two heart-cycles can be effectively distinguished from each other since the peaks corresponding to the AC event of the first heart-cycle are suppressed by the AO event of the same heart-cycle.

The afore-mentioned normal heart-related behavior is not always the case, especially when the patient suffers from irregular heart-beats such as none-effective heart-beats. In this case, the parameter γ may be increased, for instance by using γ=3, in order to achieve an effective suppression of the AC peaks.

The present invention therefore enables to correctly classify the peak detection even when irregular heart-rates occur.

In particular, the peak detection result is reliable even when the AC peak has a similar or even higher amplitude compared to the AO peak and/or the AC peak is closely followed by an AO peak of the subsequent heart-cycle in the envelope signal determined. It is understood that the afore-mentioned example involving AO and AC events is one of numerous possibilities of using the present invention. In particular, the estimated time interval may be different from the LVET.

Figure 14:
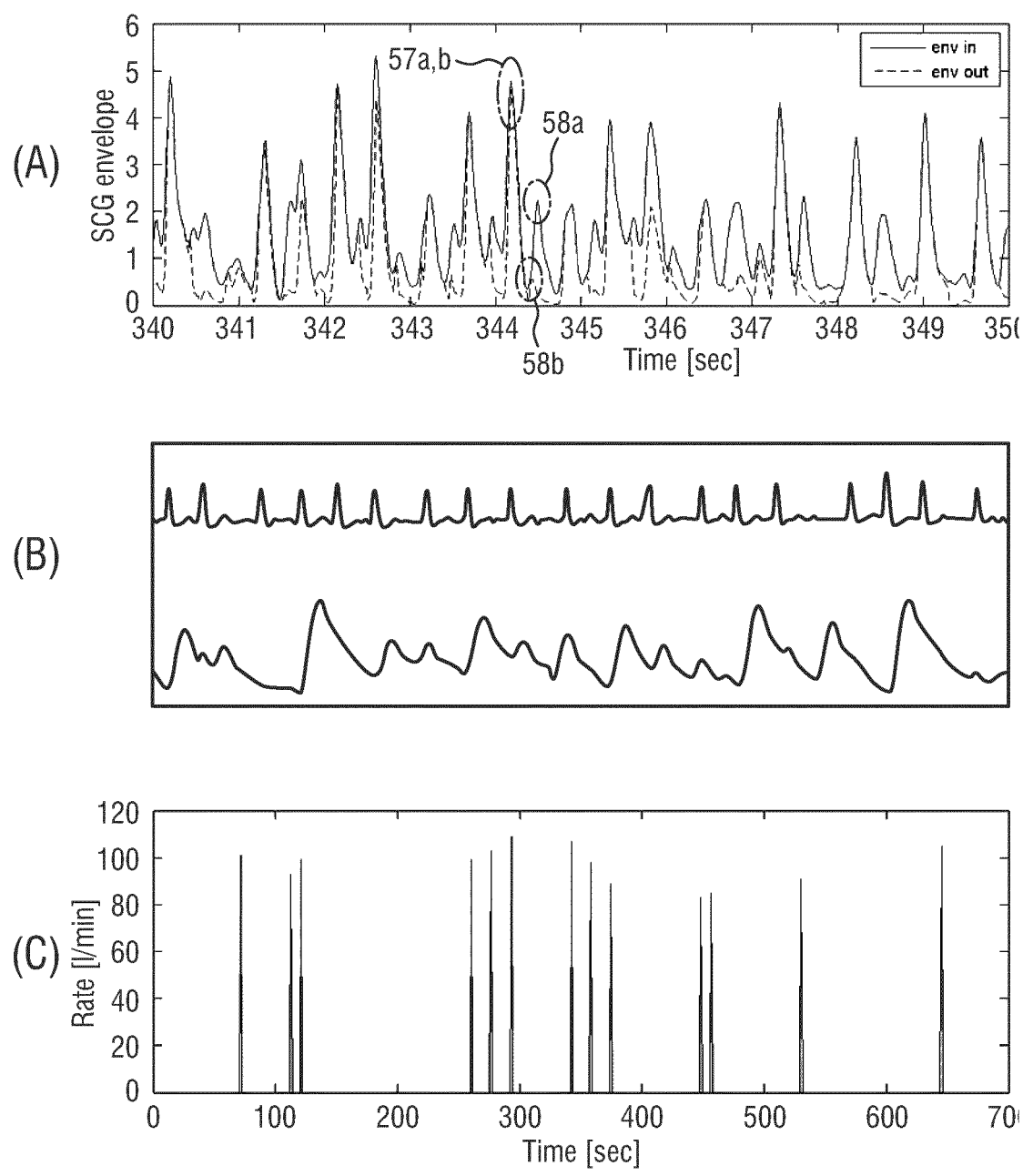
FIG. 14A-C show a first exemplary result of seismocardiogram measurements.

For the situation where the AO peak of a next heart-cycle merges with the AC peak of the current heart-cycle, as visible in FIG. 14, a further preferable embodiment of the pre-processing unit 20*iii* is presented as shown in FIG. 10' where the calculation unit 44 preferably uses a primary function to calculate the adjustment factor 43 which has the following form:

$$G = \min\{f(x, y_\Delta, y_{\Delta 2}), c\} \quad (3)$$

where f ($x$, $y_\Delta$, $y_{\Delta 2}$) is a secondary function, wherein x represents the envelope signal 41 determined from the envelope determination unit 40, $y_\Delta$ represents the positively time-shifted (i.e. delayed) envelope signal 49 provided by the estimation unit 46 and $y_{\Delta 2}$ represents the negatively time-shifted envelope signal 49' to look ahead in time. Looking ahead in time can be made possible by delaying the envelope signal 41 with the delay-unit 46' and providing the envelope signal 41 as input for the estimation unit 46. The delay-value for the delay-unit 46' can be chosen a-priori depending on the worst-case (largest) value of the delay computed by the estimation unit 46. Preferably, the primary function G is a gain function, wherein the secondary function f($x$, $y_\Delta$, $y_{\Delta 2}$) has the following form:

$$f(x, y_\Delta, y_{\Delta 2}) = \frac{x}{\gamma \cdot \max\{y_\Delta - y_{\Delta 2}, 0\} + \varepsilon} \quad (4)$$

Figure 12:
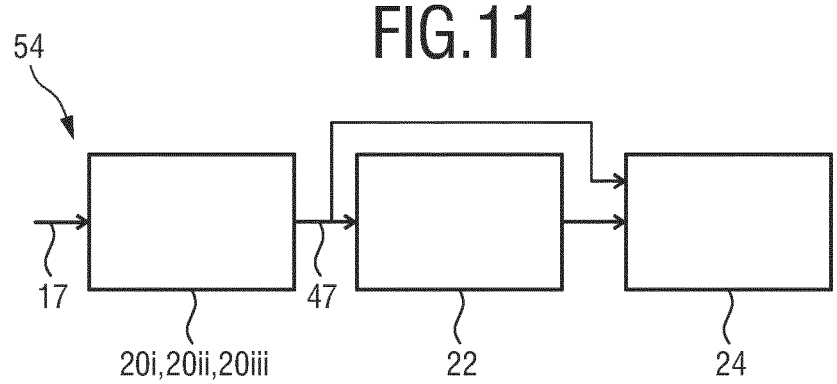
FIG. 12 shows a processing device according to another embodiment.

FIG. 12 shows an alternative processing device 54 comprising the pre-processing unit 20*i*, 20*ii* as shown in FIG. 9-8, the detection unit 22 and the classification unit 24 as shown in FIG. 4. In this way, the adjusted envelope signal 47 provided by the pre-processing unit 20*i*, 20*ii* is processed by the detection unit 22 to detect one or more peaks each associated with a cardiovascular event. The result of the peak detection is then classified by the classification unit 24, similar to the case described under reference of FIG. 4. In a preferable embodiment, the pre-processed signal 47 is provided as input for the classification unit 24.

Figure 13:
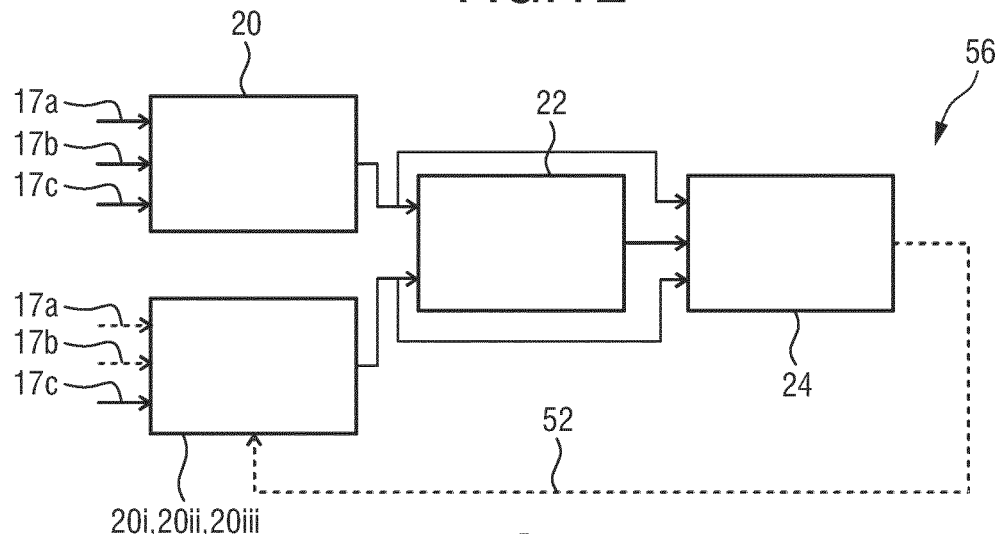
FIG. 13 shows a processing device according to a further embodiment.

FIG. 13 shows schematically another alternative processing device 56, which comprises both the pre-processing unit 20 shown in FIG. 4 and the pre-processing unit 20*i*, 20*ii* shown in FIGS. 9-8. In particular, both pre-processing units 20, 20*i*, 20*ii* are configured to interact with the peak detection unit 22 and the classification unit 24, wherein for the case, in which a peak detection and consequently the determined envelope signal from the pre-processing unit 20 is classified as "bad", the other pre-processing unit 20*i*, 20*ii* is utilized to process the SCG signal in the same way as described under reference of FIG. 9-8. In a preferable embodiment, the pre-processed signal from one or more of the pre-processing units 20, 20*i*, 20" is provided as input for the classification unit 24. Preferably, only the SCG signal 17*c* is processed by the pre-processing unit 20*i*, 20*ii*, wherein the SCG signal 17*c* may correspond to the Z-axis in a direction of the ventral-dorsal direction of the patient's body. Further preferably, the pre-processing unit 20*i*, 20*ii* is activatable by the classification unit 24, as indicated by the dashed arrow 52 in FIG. 13.

Alternatively, two processing devices may be connected one after another, one being the processing device 18 shown in FIG. 4, the other being the processing device 54 shown in FIG. 12.

Figure 15:
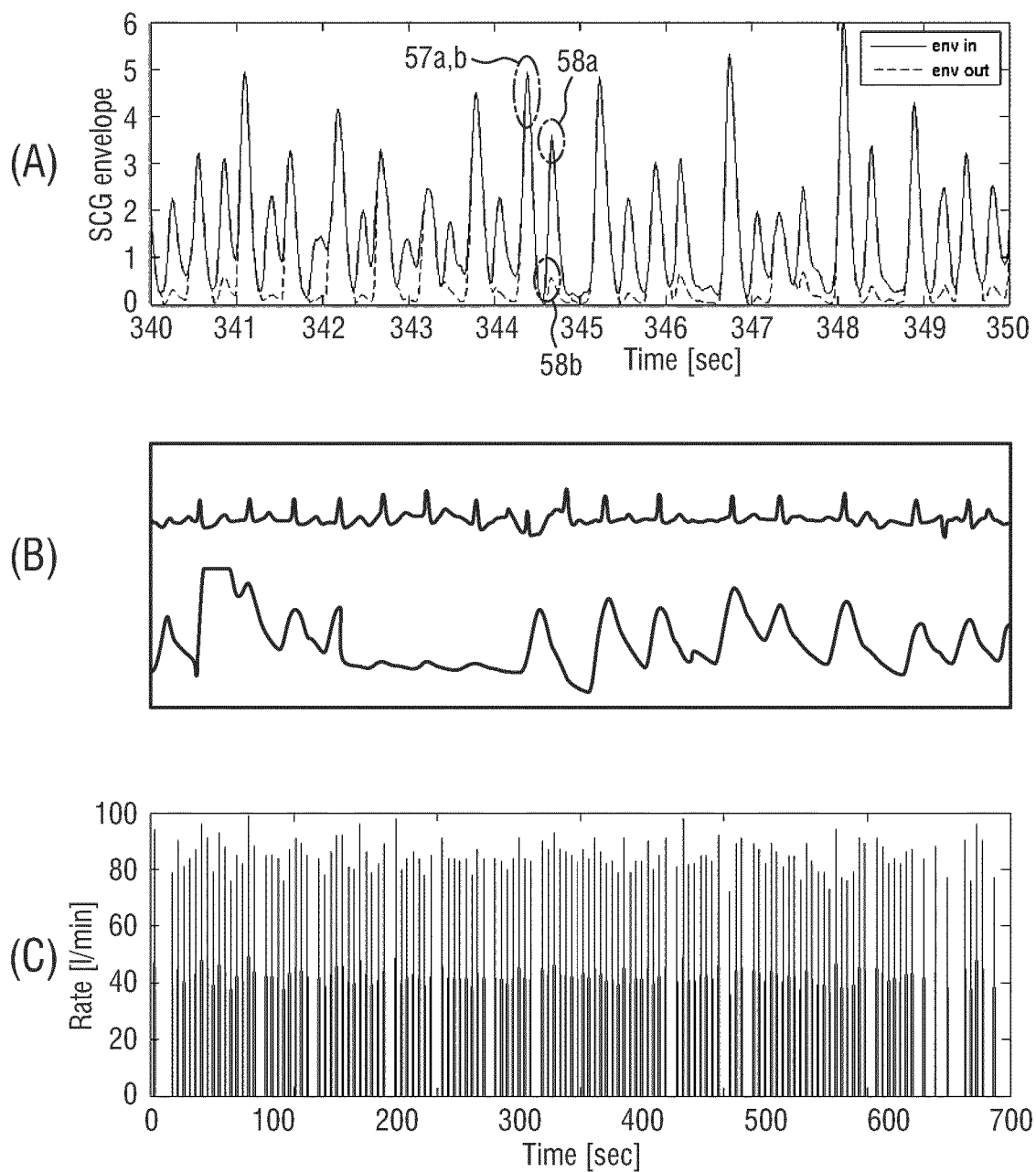
FIG. 15A-C show a second exemplary result of seismocardiogram measurements.
Figure 16:
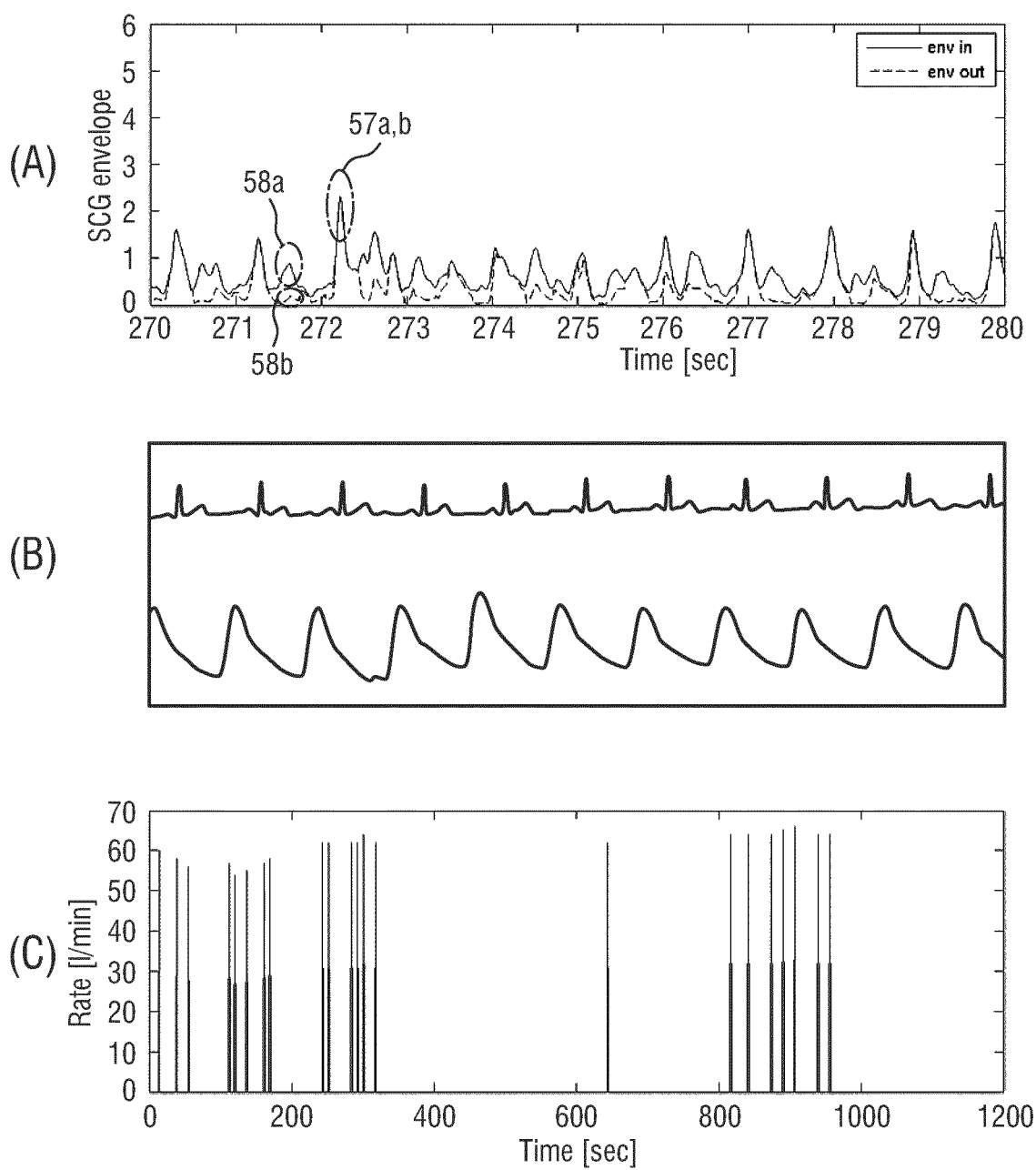
FIG. 16A-C show a third exemplary result of seismocardiogram measurements.

FIGS. 14-16 show exemplary measurement results of SCG signal processing. FIG. 14A shows a first envelope signal (solid curve) determined before being adjusted by the adjustment unit, and a second envelope signal (dashed curve) obtained after adjusting the first envelope signal using the signal adjustment unit. Both the first and the second envelope signals show a plurality of maxima-peaks. The peaks 57*a, b* as indicated by the dashed circle corresponds to an AO event, which is detected both in a first and a second envelope signal. Further, the two peaks 57*a, b* detected in the two envelope signals essentially overlap each other, meaning that the adjustment factor applied to adjust the first envelope signal at a position of this peak 57*a* in order to yield the peak 57*b* in the second envelope signal is essentially equal to one. This shows that the present invention is able effectively preserve the AO peaks in the envelope signal.

A subsequent peak 58*a, b* can also be seen in both envelope signals, wherein the peaks 58*a, b* correspond to an AC event. As can be seen in FIG. 14A, the amplitude of the peak 58*b* detected in the second envelope signal is significantly suppressed compared to the peak 58*a* detected in the first envelope signal. This shows that the present invention is able to effectively suppress AC peaks in the envelope signal.

FIG. 14B shows an ECG signal (upper graph) and a plethysmography signal (lower graph) corresponding to the SCG signal shown in FIG. 14A.

FIG. 14C shows the heart-rate derived from the second envelope signal shown in FIG. 14A over a time window of 700 s (10 s for FIG. 14A). The resolution of the heart-rate measurement is 8 s, which means that after each next 8 s, there could be a heart-rate computed. As can be seen in FIG. 14B, the so-derived heart-rate lies around 100 beats per minute, which corresponds well to the heart-rate determined from ECG for the same patient.

FIG. 15A shows essentially similar results compared to FIG. 14A. FIG. 15B shows an ECG signal (upper graph) and a plethysmography signal (lower graph) corresponding to the SCG signal shown in FIG. 15A. The heart-rate derived from the second envelope signal of FIG. 15A is shown in FIG. 15C wherein it can be seen that the so-derived heart-rate lies around 90 beats per minute, thereby corresponding well to the heart-rate determined from ECG.

FIG. 16A shows another set of first and second envelope signals, similar to those shown in FIG. 14A and FIG. 15A, wherein the signal-to-noise ratio (SNR) of FIG. 16A is significantly lower compared to FIG. 14A and FIG. 15A. Nevertheless, the heart-rate derived from the second envelope signal (dashed curve) of FIG. 16A lies around 60 beats per minute, as shown in FIG. 16C, thereby corresponding well to the heart-rate determined from ECG for the same patients, as shown in FIG. 16B (upper graph). FIG. 16B also shows a plethysmography signal (lower graph) corresponding to the SCG signal shown in FIG. 16A. This shows that the present invention is able to deliver a reliable result of heart-related vital signs even under low SNR.

Figure 17:
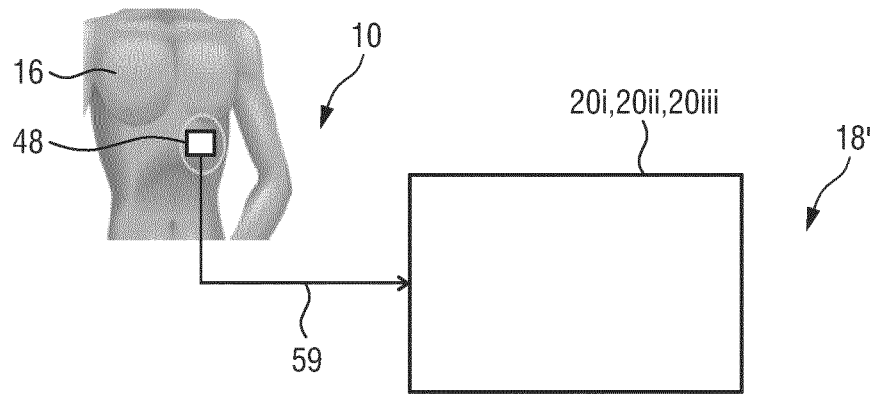
FIG. 17 shows a schematic block diagram of the monitoring system in FIG. 1.

FIG. 17 shows a monitoring system 10 comprising an accelerometer 48 attached to a patient 16 and the processing device 18' shown in FIG. 9, which comprises the pre-processing unit 20*i*, 20*ii*. The accelerometer signal 59 measured by the accelerometer 48 is processed by the processing device 20*i*, 20*ii* for monitoring heart-related vital signs of the subject 16. Preferably, the monitoring system 10 further comprises a display for displaying the processing result of the processing device 18'. In particular one or more of the following signals may be displayed: The SCG signal, the envelope signal before and/or after adjustment, one or more indicators indicating one or more peaks detected in the envelope signal, one or more labels which indicate the classification of the peak detection, and/or a heart-rate derived from the envelope signal before and/or after adjustment. Further preferably, the processing device 18' may be configured to receive and/or display an ECG signal, simultaneously to the processing result from the SCG signal or for different time interval.

Figure 18:
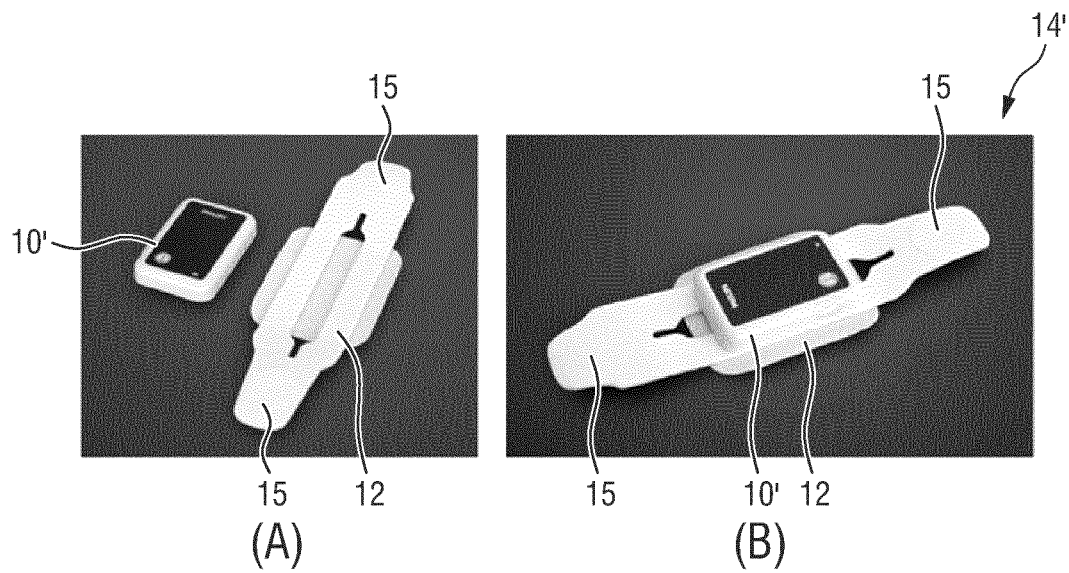
FIGS. 18A-C show a monitoring system according to another embodiment.
Figure 18:
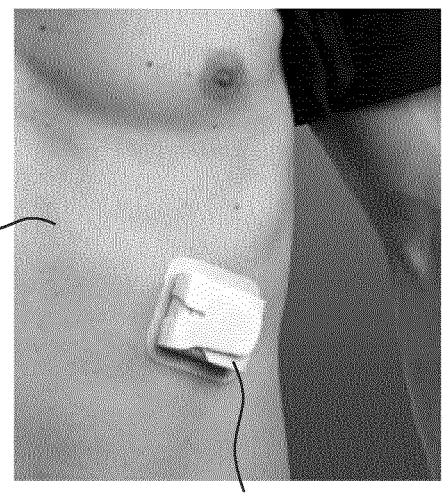

FIG. 18A shows an embodiment of the monitoring system 10', comprising a housing, wherein the accelerometer resides inside the housing and the processing device 18' is also embedded within the housing. Furthermore, heart-rates and respiration-rates are being transmitted intermittently to the central station or generic patient-monitor via a wireless connection, thereby reducing the power-consumption. The power is provided via the battery that also resides within the housing. In addition, an attaching means 12 is provided to mechanically fix the monitoring system 10', thereby forming a portable system 14' shown in FIG. 18B.

As shown in FIG. 18C, the portable system 14' can be attached to a body part of the patient 16. The closing means 15 of the attaching means 12 can be folded in order to strengthen the fixing of the housing of the monitoring system 10'. Furthermore, by the attaching means 12, a device with a depleted battery can be replaced by a new device with recharged battery without using a new disposable adhesive.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus comprising an accelerometer for processing signals for use in monitoring vital signs of a subject, comprising:
    a signal receiver configured to input an accelerometer signal of the subject in time, the accelerometer signal being related to at least one physiological event being a cardiovascular or a respiratory event of the subject and measured for at least two spatial directions, wherein the accelerometer signal is based on vibrations of the skin;
    an envelope extractor configured to determine an envelope signal of the input accelerometer signal;
    a calculator configured to calculate an adjustment factor based on an estimated time interval between a first and a second physiological event of the subject; and
    a multiplier configured to adjust the determined envelope signal by multiplying the envelope signal with the calculated adjustment factor.

2. The apparatus as claimed in claim 1, wherein the calculator is configured to use the positively and/or negatively time-shifted version of the envelope signal, shifted by the estimated time interval.

3. The apparatus as claimed in claim 2, wherein the calculator is configured to calculate the adjustment factor using a primary function, the primary function comprising a secondary function dependent on the determined envelope signal and/or the positively and/or negatively time-shifted version of the envelope signal.

4. The apparatus as claimed in claim 3, wherein the secondary function uses the determined envelope signal and/or the positively and/or negatively time-shifted version of the envelope signal as variable and at least one predefined quantity as parameter.

5. The apparatus as claimed in claim 3, wherein the primary function is configured to determine a smaller value out of a computed value of the secondary function and a constant value, the calculator being configured to determine the adjustment factor as the smaller value.

6. The apparatus as claimed in claim 1, wherein the multiplier is configured to apply a smoothing operator to the calculated adjustment factor and multiply the determined envelope signal by the smoothed adjustment factor.

7. The apparatus as claimed in claim 1, further comprising an estimation unit configured to estimate the time interval between the first and the second physiological event based on the determined envelope signal.

8. The apparatus as claimed in claim 7, wherein the estimation unit is configured to compute an auto-correlation for the determined envelope signal and/or to estimate the time interval between an aortic valve opening and an aortic valve closure of a heart-cycle of the subject.

9. The apparatus as claimed in claim 1, wherein the receiver is configured to select the accelerometer signal measured in the ventro-dorsal direction of the subject.

10. The apparatus as claimed in claim 1, wherein the envelope extractor comprises a first band-pass filter for extracting a first portion of the accelerometer signal within a frequency range from a lower threshold frequency to an upper threshold frequency, an absolute-value-generator configured to generate an absolute value of the accelerometer signal, and/or a second band-pass filter for extracting a second portion of the accelerometer signal at frequencies higher than, equal to or lower than a cutoff-frequency.

11. The apparatus as claimed in claim 1, further comprising a peak detector configured to detect in the determined envelope signal one or more maxima and/or minima each associated with a physiological event.

12. The apparatus as claimed in claim 1, further comprising a classifier configured to classify a peak detection result by deriving one or more classification features from the determined envelope signal.

13. A system for processing accelerometer signals for use in monitoring vital signs of a subject, comprising:
    the accelerometer configured to measure an accelerometer signal of the subject in time for two or more spatial directions; and the apparatus as claimed in claim 1 configured to process the accelerometer signal measured by the accelerometer.

14. A method for processing accelerometer signals for use in monitoring vital signs of a subject, comprising:
- receiving, by a signal receiver, an accelerometer signal of the subject in time, the accelerometer signal being related to at least one physiological event being a cardiovascular or a respiratory event of the subject and measured for at least two spatial directions, wherein the accelerometer signal is based on vibrations of the skin;
- determining, by an envelope extractor, an envelope signal of the input accelerometer signal;
- calculating, by a calculator, an adjustment factor based on an estimated time interval between a first and a second physiological event of the subject; and
- adjusting, by a multiplier, the determined envelope signal by multiplying the envelope signal with the calculated adjustment factor.

15. A non-transitory computer readable medium comprising program code means configured to cause a computer to carry out the steps of the method as claimed in claim 14 when said computer program is carried out on the computer.

* * * * *